United States Patent

Bolmer et al.

[11] Patent Number: 6,063,969
[45] Date of Patent: May 16, 2000

[54] PREPARATION OF 142

[75] Inventors: Michael S. Bolmer, Lower Providence; Bin Chen, Tredyffrin, both of Pa.

[73] Assignee: Elf Atochem North America, Inc., Philadelphia, Pa.

[21] Appl. No.: 09/207,494

[22] Filed: Dec. 8, 1998

[51] Int. Cl.[7] .................................................. C07C 17/08

[52] U.S. Cl. ........................... 570/167; 570/166; 570/168

[58] Field of Search ..................................... 570/166, 167, 570/168

[56] References Cited

U.S. PATENT DOCUMENTS 5,449,842  9/1995  Elsheikh .................................. 570/166

*Primary Examiner*—Alan Siegel
*Attorney, Agent, or Firm*—Stanley A. Marcus; William D. Mitchell

[57] ABSTRACT

A process for the preparation of 142 is provided, wherein 1130 is fluorinated in the gas phase in the presence of a catalyst which is a supported or unsupported fluorinated salt of one or more of chromium, iron, niobium, nickel, antimony, tin, tantalum or titanium. 142 is a known foam blowing agent.

2 Claims, No Drawings

PREPARATION OF 142

BACKGROUND OF THE INVENTION

This invention relates to the preparation of 1-chloro-2,2-difluoroethane (142) from 1,2-dichloroethene ("1130"), particularly to processes wherein said 1130 is fluorinated with hydrogen fluoride ("HF") in the gas phase in the presence of a fluorinated metal salt. 1-Chloro-2,2-difluoroethane is known to have utility as a foam blowing agent.

A. L. Henne et al, in the Journal of the American Chemical Society, Vol. 70, pages 758–760 (1948), reported that reacting 1130 with HF in the presence of a boron trifluoride catalyst yielded 1,2-dichloro-2-fluoroethane. That is, they were able to add HF to the double bond of 1130, but could not substitute F for Cl so as to form 142. Since 142 is useful as a low ozone depleting blowing agent, it would be useful to have a process for readily preparing the same.

BRIEF SUMMARY OF THE INVENTION

A process for preparing 142 is provided, which process comprises (a) contacting 1130 with HF in the gas phase in the presence of a catalyst which is a supported or unsupported fluorinated salt of one or more of chromium, iron, niobium, nickel, antimony, tin, tantalum and titanium (preferably a supported fluorinated salt of antimony) under conditions sufficient to produce 142, and (b) recovering 142 from the resultant reactant mixture.

DETAILED DESCRIPTION

It has now been discovered that 142 can be successfully prepared from 1130 in good yields by using as the catalyst a supported or unsupported fluorinated salt of one or more of chromium, iron, niobium, nickel, antimony, tin, tantalum and titanium, preferably a fluorinated salt of antimony. Useful catalyst supports include fluorinated $Al_2O_3$, activated carbon, graphite or fluorinated graphite. The initial catalyst salts can be formed from chlorides, nitrates, and the like, while the initial catalyst support can be, for example, $Al_2O_3$, since the catalyst and support are fluorinated with HF either during an initial catalyst activation or during the course of the reaction. HF activation is well known in the art, typically involving a procedure wherein HF and air or nitrogen are fed over a heated catalyst bed for about 18 hours.

Typical conditions for carrying out the reaction are a temperature between 100° C. and 380° C. (preferably between 120° C. and 250° C.), a pressure of between 0 psig and 400 psig (preferably between 50 psig and 200 psig), a feed ratio of HF to 1130 of between 2 and 20 (preferably between 5 and 10) and a contact time of between 1 and 100 seconds (preferably between 10 and 35 seconds).

The hydrogen chloride (HCl) by-product may be removed by distillation or absorption into water or caustic solution. The unreacted HF can be separated by distillation, absorption into water or caustic solution, phase separation or by use of a semipermeable membrane. Other organic by-products may be separated by distillation. Unsaturated organic by-products may be more easily separated by first reacting the product mixture with chlorine or bromine before distillation.

The practice of the invention is illustrated in more detail in the following non-limiting examples:

EXAMPLE 1

Chromium oxide ($Cr_2O_3$) catalyst (20 cc, 27 g) was activated at 380° C. by cofeeding a mixture of HF (6.6 g/h) and air (100 cc/min) over the catalyst bed for 18 hours. 1130 and HF, in a molar ratio of HF:1130 of about 6.5:1 (10.1 g/h of HF and 0.1 cc/min of 1130), were then fed to the reactor in the gas phase at 220° C. and 150 psig for a contact time of 34 seconds, resulting in 88.3% conversion of the 1130, with selectivity being 84.2% for the desired 142. Analysis was done by a gas chromatograph, equipped with a thermal conductivity detector and a flame ionization detector.

EXAMPLE 2

30 cc of antimony chloride ($SbCl_5$) catalyst supported on activated carbon was activated at 50° C. by cofeeding a mixture of HF (6.6 g/h) and nitrogen (100 cc/min) over the catalyst bed for 18 hours. 1130 and HF, in a molar ratio of HF:1130 of about 6.5:1 (10.1 g/h of HF and 0.1 cc/min of 1130), were then fed to the reactor in the gas phase at 120° C. and 120 psig for a contact time of 34 seconds, resulting in 95% conversion of the 1130, with selectivity being 94.9% for the desired 142. Analysis was done as in Example 1.

What is claimed is:

1. A process for preparing 1-chloro-2,2-difluoroethane which comprises (a) contacting 1,2-dichloroethene with hydrogen fluoride in the gas phase in the presence of a catalyst which is a supported or unsupported fluorinated salt of one or more of chromium, iron, niobium, nickel, antimony, tin, tantalum or titanium under conditions sufficient to produce 1-chloro-2,2-difluoroethane; and (b) recovering 1-chloro-2,2-difluoroethane from the resultant reaction mixture in step (a).

2. A process as in claim 1 wherein the catalyst is a supported fluorinated salt of antimony.

* * * * *